United States Patent [19]

Hamley et al.

[11] Patent Number: 6,046,191
[45] Date of Patent: Apr. 4, 2000

[54] COMBINATION

[75] Inventors: Peter Hamley, Thrussington; Alan Tinker, Loughborough, both of United Kingdom

[73] Assignee: Astra Pharmaceuticals Ltd., Herts., United Kingdom

[21] Appl. No.: 09/171,801

[22] PCT Filed: Oct. 5, 1998

[86] PCT No.: PCT/SE98/01792

§ 371 Date: Oct. 26, 1998

§ 102(e) Date: Oct. 26, 1998

[87] PCT Pub. No.: WO99/18960

PCT Pub. Date: Apr. 22, 1999

[30] Foreign Application Priority Data

Oct. 10, 1997 [SE] Sweden .................................. 9703693

[51] Int. Cl.⁷ ............................ A61K 31/47; A61K 45/06
[52] U.S. Cl. ..................................... 514/232.8; 514/233.5; 514/233.8; 514/235.2; 514/300; 514/301; 514/307; 514/309; 514/310

[58] Field of Search .............................. 514/232.8, 233.5, 514/233.8, 235.2, 300, 301, 307, 309, 310

[56] References Cited

FOREIGN PATENT DOCUMENTS

WO 9641626  12/1996  WIPO .
WO 9641645  12/1996  WIPO .
WO 9729774   8/1997  WIPO .

OTHER PUBLICATIONS

J. Med. Chem., vol. 40, 1997, Lazer et al, "Effect of Structural Modification of Enol–Carboxamide–type Nonsteroidal Antiinflammatory Drugs on COX–2/COX–1 Selectivity", pp. 980–989, Apr. 1997.

Primary Examiner—Frederick Krass
Attorney, Agent, or Firm—Nixon & Vanderhye

[57] ABSTRACT

The invention relates to the co-administration of an inhibitor of induced nitric oxide synthase and an inhibitor of cyclooxygenase-2 for the treatment of inflammation and inflammatory disorders.

10 Claims, No Drawings

COMBINATION

This application is a 371 of PCT/SE98/01792, filed Oct. 5, 1998.

The present invention relates to the co-administration of an inhibitor of induced nitric oxide synthase and an inhibitor of cyclooxygenase-2 for the treatment of inflammation and inflammatory disorders, such as arthritis, inflammatory bowel disease and CNS inflammatory disorders.

The excessive production of nitric oxide (NO) has been implicated in immune and inflammatory responses and as an important and novel mechanism in the pathology of a variety of chronic inflammatory diseases (Moncada S. et al, *Pharmacol. Rev.*, 1991, 43, 109). The role of NO, as either a beneficial physiological mediator, or as pathological cytotoxic radical, is largely determined by the level and extent of synthesis. Under physiological conditions only low levels of NO are required for effector functions, whereas excessive NO production may be detrimental and pathological.

The synthesis of NO from the semi-essential amino acid L-arginine is catalysed by three different enzyme isoforms: endothelial NOS (eNOS) and neuronal NOS (nNOS) are constitutively expressed, calcium dependent enzymes and play a major role in normal physiology. The third major NOS isoform, inducible NOS (iNOS) is not expressed under physiological conditions but requires induction. Inflammatory stimuli, such as endotoxin and the cytokines interleukin-1 (IL-1), tumour necrosis factor-$\alpha$ (TNF$\alpha$) or interferon gamma (INF$\gamma$), induce de novo formation of a calcium independent NOS in a variety of cells, including epithelial cells, macrophages and neutrophils. The inducible NOS (iNOS) produces much greater amounts of NO for longer periods compared to the constitutive enzymes.

There is considerable evidence for an important role for iNOS in inflammation. The excessive NO production following induction of NO synthase plays an important role in the vascular permeability in intestinal inflammation produced by endotoxin. Inhibitors of iNOS attenuate the increase in plasma leakage (Boughton-Smith N. K. et al, *Eur. J. Pharmacol.*, 1990, 191, 485). Inhibitors of iNOS reduce plasma leakage produced in zymosan peritonitis and by carrageenan in the rat paw and air pouch, in which there are increases in iNOS activity (Ialenti A., *Eur. J Pharmacol.*, 1992, 211, 177; Salvamini D. et al, *J. Clin. Invest.*, 1995, 96, 301; Salvemini D. et al, *Br. J. Pharmacol.*, 1996, 118, 829; Boughton-Smith N. K. and Ghelani A., *Inflamm. Res.*, 1995, Suppl. 2, S149). In rat adjuvant arthritis there are increases in plasma nitrite and NO production by peritoneal macrophages and immunoreactive iNOS is localised to synovial tissue. Paw swelling, loss in weight gain, synovial inflammation and cartilage degradation are reduced by the non-selective NOS inhibitors L-NAME and L-NMMA (Ialenti A. et al, *Br. J. Pharmacol.*, 1993, 110, 701; Stefanovic-Racic M., *Arthritis and Rheumatism*, 1994, 37, 1062; Stefanovic-Racic M. et al, *Rheumatol.*, 1995, 22, 1922). Inhibitors of NOS also have beneficial effects in a rat model of arthritis induced by streptococcal cell wall (McCartney-Frances N., *J. Exp. Med.*, 1993, 178, 749) and in the spontaneous arthritis and nephritis produced in MLR lpr/lpr mice, in which there is also evidence of iNOS induction (Weinberg J. B., *J Exp. Med.*, 1994, 179, 651). There are also increases in NOS activity in animal models of inflammatory bowel disease and an inhibitor of NOS ameliorates guinea-pig model ileitis (Boughton-Smith N. K. et al, *Agents and Actions*, 1994, 41, 223; Miller M. J. S., *J. Pharmacol. Exp. Ther.*, 1993, 264, 11).

In clinical studies there are increases in the production of NO and in iNOS expression in a variety of chronic inflammatory diseases, such as rheumatoid and osteoarthritis (Farrell A. J. et al, *Ann Rheum. Dis.*, 1992, 51, 1219; Grabowski P. S. et al, *Arth. & Rheum.*, 1996, 39, 643; Stichtenoth D. O. et al, *Ann of the Rheumatic Diseases*, 1995, 54, 820; McInnes I. B. et al, *J. Exp. Med.*, 1996, 184, 1519), inflammatory bowel disease (Boughton-Smith N. K. et al, *Lancet*, 1993, 342, 338; Lundberg J. O. N. et al, *Lancet*, 1994, 344, 1673; Middleton S. J. et al, *Lancet*, 1993, 341, 465), psoriasis (Rowe A. et al, *Lancet*, 1994, 344, 1371; Bruch-Gerharz D. et al, *J. Exp. Med.*, 1996, 184, 2007) and asthma (Hamid, Q. et al, *Lancet*, 1993, 342, 1510; Barnes J. and Liew F. Y., *Immunol. Today*, 1995, 16, 128) and iNOS is implicated as a major pathological factor in these chronic inflammatory diseases. Thus, there is considerable evidence that inhibition of excessive NO production by iNOS will be anti-inflammatory. Since the production of NO from eNOS and nNOS is involved in normal physiology, it is important that any NOS inhibitor used therapeutically for treating inflammation is selective for iNOS. Such an inhibitor will inhibit the excessive production of NO by iNOS without effecting the modulation of blood pressure produced by NO production from eNOS or the non-adrenergic non-cholinergic neuronal transmission produced by NO from nNOS.

The recent discovery of an inducible isoform of cyclooxygenase (COX-2) has provided a specific target for inhibition of inflammatory prostaglandin synthesis while leaving the physiological actions of prostaglandins formed by constitutive cyclooxygenase (COX-1) intact (Fu et al, *J. Biol. Chem.*, 1989, 265, 16740; DeWitt D., *Biophys. Acta*, 1991, 1083, 121; Masferrer J. L. and Seibert, *Receptor*, 1994, 94, 17). Prostaglandins play an important role in inflammation, for example in both the pain and swelling associated with arthritis. The commonly used cyclooxygenase inhibitors or non-steroid anti-inflammatory drugs (NSAIDs) are non-selective in that they reduce prostaglandins involved in inflammatory pain and swelling but also inhibit the physiological prostaglandin formation which is required particularly for maintenance of gastrointestinal integrity. A number of selective COX-2 inhibitors have been described which are anti-inflammatory in a variety of animal models but which, unlike non-selective COX inhibitors, do not produce gastrointestinal pathology.

Since both iNOS and COX-2 inhibitors are selective for the enzyme isoforms induced in inflammation which produce NO and prostaglandins respectively, and will not effect the constitutive enzymes involved in normal physiology, the combination will have a substantially reduced level of adverse side effects associated with NSAIDs and also anti-inflammatory glucocorticoids, which inhibit the induction of both enzymes (Radomski M. V. et al, *Proc. Natl. Acad. Sci. USA*, 1990, 87, 10043; Masferrer J. L. et al, *J. Clin. Invest.*, 1990, 86, 1375).

Compounds that selectively inhibit COX-2 have been described in U.S. Pat. Nos. 5,380,738; 5,344,991; 5,466,823; 5,434,178; 5,474,995; 5,510,368; 5,521,207 and 5,604,260.

Compounds that selectively inhibit iNOS have been described in U.S. Pat. Nos. 5,132,453 and 5,273,875.

Combination therapies of NSAIDs with other drugs targeted at different mechanisms are known in the art. A combination of the analgesic diflunisal and an antispasmodic compound has been described (Basmajian J., *Spine*, 1989, 14, 438). Also, a combination of ibuprofen with an antispasmodic to reduce morning stiffness in primary fibromyaglia syndrome (Fossaluzza V. and DeVita S., *Int. J. Clin. Pharm. Res.*, 1992, 12, 99) and a combination of tetracycline with flurbiprofen for the treatment of rheumatoid arthritis (Greenwald R. et al, *J. Rheumatol.,* 1992, 19, 927) are known.

However, COX-2 inhibitors (and other NSAIDs) do not have complete efficacy and do not completely overcome the inflammatory condition being treated, even at optimal doses. There is therefore a need to improve the efficacy of COX-2 inhibitors. It has now been found that the efficacy of a COX-2 inhibitor can be improved if it is combined with a iNOS inhibitor, and as a result inflammatory diseases may be treated with a combination of an iNOS inhibitor and a COX-2 inhibitor. Although it has been said that some of the inflammatory actions of iNOS are dependent on the secondary activation of COX and an increase in prostaglandin formation (Salvemini D. et al, *Proc. Nat. Acad. Sci. USA,* 1993, 90, 7240; Salvemini et al, *J Clin. Invest.,* 1995, 96, 301) it is believed that a combination of selective inhibitors of iNOS and COX-2 will lead to a substantially greater anti-inflammatory efficacy compared with the efficacy of each agent alone. By inhibiting iNOS and COX-2 at inflammatory sites the combination will result in a greater and more complete reduction in the severity of inflammation in a variety of inflammatory diseases and inflammation related disorders.

In a first aspect the invention provides a combination of an iNOS inhibitor and a COX-2 inhibitor or pharmaceutically acceptable salts thereof for treating inflammation, inflammatory disease and inflammatory related disorders.

Preferred iNOS inhibitors for use in the combinations of the invention include compounds known from WO 97/38977, that is to say, compounds of formula (I):

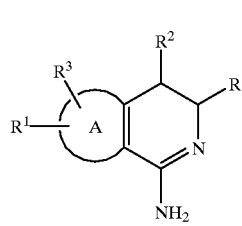

(I)

wherein:

R represents (i) phenyl, benzothiazolyl or a six membered heterocyclic aromatic ring containing 1 to 3 nitrogen atoms, which phenyl, benzo ring of the benzothiazolyl or heterocyclic aromatic ring is optionally substituted by $C_{1-6}$ alkyl, $C_{1-6}$ alkoxy, halogen, hydroxy, thio$C_{1-6}$ alkyl, benzyloxy, or a group —$Q(CH_2)_pNR^4R^5$; or (ii) $C_{1-8}$ alkyl, $C_{3-8}$ cycloalkyl, $C_{2-8}$ alkynyl, piperidyl, $C_{7-14}$ phenylalkyl, which alkyl, cycloalkyl, alkynyl, or piperidyl is optionally substituted by a group —$(CH_2)_p NR^4R^5$, the phenylalkyl being optionally substituted by a group —$(CH_2)_pNR^4R^5$, $C_{1-6}$ alkyl, $C_{1-6}$ alkoxy, halogen or nitro; or (iii) a 5 membered heterocyclic aromatic ring containing 1 to 3 heteroatoms independently selected from O, N or S, optionally substituted by $C_{1-6}$ alkyl, $C_{7-14}$ phenylalkyl or halogen; or (iv) hydrogen or $C_{7-14}$ phenylalkynyl;

Q represents O, $NR^6$ or a bond;

$R^1$ represents hydrogen, $C_{1-6}$ alkyl, $C_{1-6}$ alkoxy, trimethylsilyl or halogen;

$R^2$ represents hydrogen, $C_{1-6}$ alkyl or phenyl optionally substituted by $C_{1-6}$ alkyl, $C_{1-6}$ alkoxy, halogen or hydroxy;

$R^3$ represents hydrogen or halogen;

$R^4$, $R^5$ and $R^6$ independently represent hydrogen or $C_{1-6}$ alkyl, or —$NR^4R^5$ together represents piperidyl, pyrrolidinyl or morpholinyl;

p represents an integer 1 to 5; and

A represents a thieno or benzo ring;

or a pharmaceutically acceptable salt thereof.

Preferably R is ethynyl, cyclopropyl, fluorophenyl, benzyloxyphenyl, thiomethylphenyl, methylphenyl, methoxyphenyl, chlorophenyl, furyl, thienyl, pyridyl, phenylethynyl, aminopropyloxyphenyl, aminoethylphenyl, aminopropylphenyl, thiazolyl, imidazolyl, methyl, ((dimethylamino)methyl)phenyl, propynyl, butylethynyl, benzylpyrrolyl, methylpyrrolyl, ethyl, cyclobutyl, hydroxyphenyl orpropyl. More preferably R is ethyl, propyl, cyclopropyl, cyclobutyl, ethynyl or 1-propynyl.

Preferably $R^1$ and $R^3$ are hydrogen or halo.

Preferably $R^2$ is hydrogen.

More preferably the compound of formula (I) is selected from:

1-amino-3-(2-fluorophenyl)-3,4-dihydroisoquinoline; or 1-amino-3-phenyl-3,4-dihydroisoquinoline; or 1-amino-3-(4-(benzyloxy)phenyl)-3,4-dihydroisoquinoline; or 1-amino-3-(4-(methylthio)phenyl)-3,4-dihydroisoquinoline; or 1-amino-3-(4-(methyl)phenyl)-3,4-dihydroisoquinoline; or 1-amino-3-(3-(methyl)phenyl)-3,4-dihydroisoquinoline; or 1-amino-3-(4-(methoxy)phenyl)-3,4-dihydroisoquinoline; or 1-amino-5-methoxy-3-phenyl-3,4-dihydroisoquinoline; or 1-amino-3-(2-(chloro)phenyl)-3,4-dihydroisoquinoline; or 1-amino-3-(3-(chloro)phenyl)-3,4-dihydroisoquinoline; or 1-amino-3-(4-(chloro)phenyl)-3,4-dihydroisoquinoline; or 1-amino-5-chloro-3-phenyl-3,4-dihydroisoquinoline; or 1-amino-8-chloro-3-phenyl-3,4-dihydroisoquinoline; or 1-amino-3-(4-(fluoro)phenyl)-3,4-dihydroisoquinoline; or 1-amino-3-(3-(fluoro)phenyl)-3,4-dihydroisoquinoline; or 1-amino-5-fluoro-3-phenyl-3,4-dihydroisoquinoline; or 1-amino-8-fluoro-3-phenyl-3,4-dihydroisoquinoline; or 1-amino-6-bromo-3-phenyl-3,4-dihydroisoquinoline; or 1-amino-3-(2-(methyl)phenyl)-3,4-dihydroisoquinoline; or 1-amino-7-methyl-3-phenyl-3,4-dihydroisoquinoline; or 1-amino-5-methyl-3-phenyl-3,4-dihydroisoquinoline; or 1-amino-3-(2-furyl)-3,4-dihydroisoquinoline; or 1-amino-3-(3-furyl)-3,4-dihydroisoquinoline; or 1-amino-3-(2-thienyl)-3,4-dihydroisoquinoline; or 1-amino-3-(3-thienyl)-3,4-dihydroisoquinoline; or 1-amino-8-chloro-3-(2-furyl)-3,4-dihydroisoquinoline; or 1-amino-3-(3-pyridyl)-3,4-dihydroisoquinoline; or 1-amino-3-(4-pyridyl)-3,4-dihydroisoquinoline; or
1-amino-3-cyclopropyl-3,4-dihydroisoquinoline; or
1-amino-3-(2-(dimethylamino)methyl)phenyl-3,4-dihydroisoquinoline; or
1-amino-3-(3-(dimethylamino)methyl)phenyl-3,4-dihydroisoquinoline; or
1-amino-3-(2-benzothiazolyl)-3,4-dihydroisoquinoline; or
1-amino-8-chloro-3-(4-fluorophenyl)-3,4-dihydroisoquinoline; or
1-amino-3-(phenylethynyl)-3,4-dihydroisoquinoline; or
1-amino-8-methyl-3-phenyl-3,4-dihydroisoquinoline; or
1-amino-5-fluoro-3-(4-fluorophenyl)-3,4-dihydroisoquinoline; or
1-amino-8-fluoro-3-(4-fluorophenyl)-3,4-dihydroisoquinoline; or
1-amino-5,8-difluoro-3-(4-fluorophenyl)-3,4-dihydroisoquinoline; or
1-amino-6-fluoro-3-(4-fluorophenyl)-3,4-dihydroisoquinoline; or
1-amino-7-fluoro-3-(4-fluorophenyl)-3,4-dihydroisoquinoline; or
1-amino-3-ethynyl-3,4-dihydroisoquinoline; or
1-amino-3-(4-(3-aminopropyloxy)phenyl)-3,4-dihydroisoquinoline; or
1-amino-3-(3-(2-aminoethyl)phenyl)-3,4-dihydroisoquinoline; or
1-amino-3-(4-(2-aminoethyl)phenyl)-3,4-dihydroisoquinoline; or
1-amino-3-(3-(3-aminopropyl)phenyl)-3,4-dihydroisoquinoline; or
1-amino-3-(2-thiazolyl)-3,4-dihydroisoquinoline; or
1-amino-3-(2-imidazolyl)-3,4-dihydroisoquinoline; or
1-amino-3-(4-piperidyl)-3,4-dihydroisoquinoline; or
1-amino-3-methyl-3,4-dihydroisoquinoline; or
1-amino-3-(4-hydroxyphenyl)-3,4-dihydroisoquinoline; or
7-amino-5-phenyl-4,5-dihydrothieno[2,3-c]pyridine; or
7-amino-5-(3-pyridyl)-4,5-dihydrothieno[2,3-c]pyridine; or
7-amino-5-cyclopropyl-4,5-dihydrothieno[2,3-c]pyridine; or
7-amino-5-(3-furyl)-4,5-dihydrothieno[2,3-c]pyridine; or
7-amino-5-(2-furyl)-4,5-dihydrothieno[2,3-c]pyridine; or
7-amino-5-(2-thienyl)-4,5-dihydrothieno[2,3-c]pyridine; or
7-amino-5-(1-benzyl-2-pyrrolyl)-4,5-dihydrothieno[2,3-c]pyridine; or
7-amino-5-(1-methyl-2-pyrrolyl)-4,5-dihydrothieno[2,3-c]pyridine; or
7-amino-5-ethynyl-4,5-dihydrothieno[2,3-c]pyridine; or
7-amino-5-propynyl-4,5-dihydrothieno[2,3-c]pyridine; or
7-amino-5-(2-thiazolyl)-4,5-dihydrothieno[2,3-c]pyridine; or
7-amino-5-(3,3-dimethylbutynyl)-4,5-dihydrothieno[2,3-c]pyridine; or
7-amino-5-(phenylethynyl)-4,5-dihydrothieno[2,3-c]pyridine; or
7-amino-5-(cyclobutyl-)-4,5-dihydrothieno[2,3-c]pyridine; or
7-amino-5-ethynyl-2-methyl-4,5-dihydrothieno[2,3-c]pyridine; or
7-amino-5-ethyl-4,5-dihydrothieno[2,3-c]pyridine; or
7-amino-5-propyl-4,5-dihydrothieno[2,3-c]pyridine; or
4-amino-6-phenyl-6,7-dihydrothieno[3,2-c]pyridine; or
4-amino-6-ethynyl-6,7-dihydrothieno[3,2-c]pyridine; or
4-amino-6-cyclopropyl-6,7-dihydrothieno[3,2-c]pyridine; or
7-amino-4,5-dihydrothieno[2,3-c]pyridine; or
4-amino-6,7-dihydrothieno[3,2-c]pyridine;
or pharmaceutically acceptable salts thereof.

Particularly preferred compounds include:
1-amino-8-fluoro-3-phenyl-3,4-dihydroisoquinoline; or
1-amino-3-(2-furyl)-3,4-dihydroisoquinoline; or
1-amino-3-(3-furyl)-3,4-dihydroisoquinoline; or
1-amino-3-(2-thienyl)-3,4-dihydroisoquinoline; or
1-amino-3-(3-thienyl)-3,4-dihydroisoquinoline; or
1-amino-8-chloro-3-(2-furyl)-3,4-dihydroisoquinoline; or
1-amino-3-cyclopropyl-3,4-dihydroisoquinoline; or
1-amino-8-fluoro-3-(4-fluorophenyl)-3,4-dihydroisoquinoline; or
1-amino-5,8-difluoro-3-(4-fluorophenyl)-3,4-dihydroisoquinoline; or
1-amino-3-ethynyl-3,4-dihydroisoquinoline; or
7-amino-5-cyclopropyl-4,5-dihydrothieno[2,3-c]pyridine; or
7-amino-5-phenyl-4,5-dihydrothieno[2,3-c]pyridine; or
7-amino-5-(3-furyl)-4,5-dihydrothieno[2,3-c]pyridine; or
7-amino-5-(2-furyl)-4,5-dihydrothieno[2,3-c]pyridine; or
7-amino-5-(2-thienyl)-4,5-dihydrothieno[2,3-c]pyridine; or
7-amino-5-(1-methyl-2-pyrrolyl 4,5-dihydrothieno[2,3-c]pyridine; or
7-amino-5-ethynyl-4,5-dihydrothieno[2,3-c]pyridine; or
7-amino-5-propynyl-4,5-dihydrothieno[2,3-c]pyridine; or
7-amino-5-(cyclobutyl)-4,5-dihydrothieno[2,3-c]pyridine; or
7-amino-5-ethyl-4,5-dihydrothieno[2,3-c]pyridine; or
7-amino-5-propyl-4,5-dihydrothieno[2,3c]pyridine; or
4-amino-6-ethynyl-6,7-dihydrothieno[3,2-c]pyridine; or
4-amino-6-cyclopropyl-6,7-dihydrothieno[3,2-c]pyridine; or
4-amino-6-phenyl-6,7-dihydrothieno[3,2-c]pyridine;
or pharmaceutically acceptable salts thereof.

Preferred COX-2 inhibitors for use in the combinations of the invention include those disclosed in WO 96/41626, in particular the compound known as Celecoxib (Searle—compound 2 below). Other preferred COX-2 inhibitors for use in the combinations of the invention include those disclosed in Drugs of the Future, 1997, 22, pages 711–714 which document is incorporated herein by reference, namely (1) Meloxicam, (3) L-745337 (Merck), (4) MK-966 (Merck), (5) L-768277 (Merck), GR-253035 (Glaxo-Welicome), JTE-522 (Japan Tobacco), (8) RS-57067-000 (Roche), (9) SC-58125 (Searle), (10) SC-078 (Searle), (11) PD-138387 (Warner-Lambert), NS-398 (Taisho), flosulide and (12) PD-164387 (Warner-Lambert).

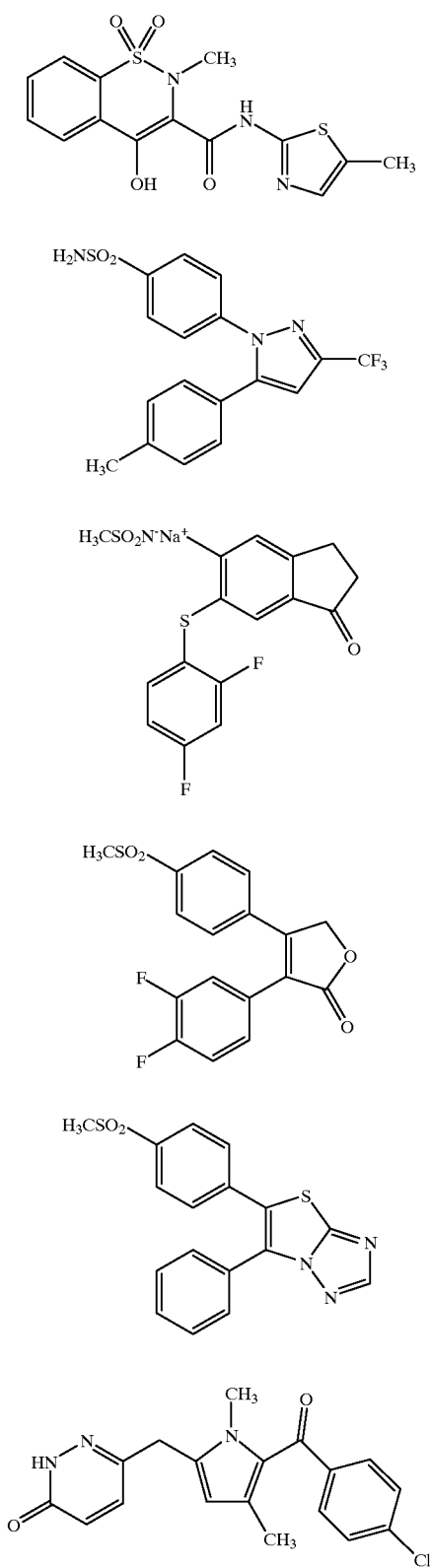
More preferably the COX-2 inhibitor is Celecoxib or MK-966:

-continued

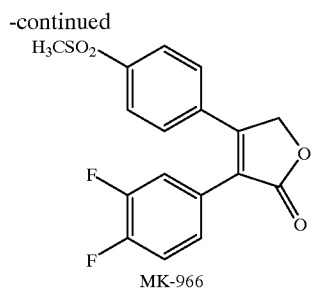
MK-966

The combination of an iNOS inhibitor and a COX-2 inhibitor would be used to treat other inflammation associated disorders, such as an analgesic for pain and headaches or as an antipyretic for the treatment of fever. The combination would be used to treat arthritis and other skeletal muscular conditions, for example rheumatoid arthritis, osteoarthritis, spondyloerthritis, gouty arthritis, juvenile arthritis and systemic lupus erythematosus and tendinitis. The combinations would also be used to treat asthma, chronic obstructive pulmonary disease, bronchitis, adult respiratory distress syndrome and other conditions of pulmonary inflammation such as cystic fibrosis and those associated with viral infection. The combination would also be used to treat inflammatory conditions of the skin such as psoriasis, eczema, dermatitis and burns. The combination would also be used to treat inflammatory diseases of the gastrointestinal tract such as inflammatory bowel disease (Crohn's disease and ulcerative colitis), gastritis and peptic ulceration and also irritable bowel syndrome. In addition the combination would also be useful in the treatment of cancer, including colorectal cancer and breast cancer. The combination would also be useful in the treatment of inflammatory conditions of the cardiovascular system such as atherosclerosis, periarteritis nodosa and migraine.

The invention therefore provides a combination as described herein for use in therapy, that is for both treatment and prophylaxis of a disease.

Prophylaxis is expected to be particularly relevant to the treatment of persons who have suffered a previous episode of, or are otherwise considered to be at increased risk of, the disease or condition in question. Persons at risk of developing a particular disease or condition generally include those having a family history of the disease or condition, or those who have been identified by genetic testing or screening to be particularly susceptible to developing the disease or condition.

The invention also provides a method of treatment or prophylaxis of an inflammatory disease in a person, which method comprises administering to the person a therapeutically effective amount of the combination.

By the term "combination" is meant any pharmaceutical composition in which the iNOS inhibitor and the COX-2 inhibitor are administered in a single dosage unit, for example a single tablet or capsule containing a fixed ratio of the two active ingredients, as well as combination therapy in which the iNOS inhibitor and the COX-2 inhibitor are administered in separate dosages, that is to say, administration of each agent simultaneously or sequentially.

In a further aspect the invention relates to a kit comprising one or more unit doses of an iNOS inhibitor or a pharmaceutically acceptable salt thereof and one or more unit doses of a COX-2 inhibitor or a pharmaceutically acceptable salt thereof. Such kits can, for example, be in the form of blister packs containing each medicament in separate unit doses.

For the above mentioned therapeutic indications, the dosage administered will, of course, vary with the compound employed, the mode of administration and the treatment desired. However, in general, satisfactory results are obtained when the compounds are administered at a daily dosage of the solid form of between 1 mg and 2000 mg per day.

The combinations of the invention may be used on their own, or preferably as a pharmaceutical composition in which the compounds or derivatives are in admixture with a pharmaceutically acceptable adjuvant, diluent or carrier. For example in a form appropriate for enteral or parenteral administration. The pharmaceutical composition preferably comprises less than 80% and more preferably less than 50% of the compound or derivative. Examples of suitable adjuvants, diluents and carriers are well known to a person skilled in the art and include microcrystalline cellulose, calcium phosphate, diatomaceous earth, a sugar such as lactose, dextrose or mannitol, talc, stearic acid, starch, sodium bicarbonate and/or gelatin.

According to a further aspect of the invention there is provided a pharmaceutical composition comprising a combination of an iNOS and COX-2 inhibitor as hereinbefore defined in association with a pharmaceutically acceptable adjuvant, diluent or carrier.

According to a further aspect of the invention there is thus provided the use of a combination of an iNOS and COX-2 inhibitor as hereinbefore defined or a pharmaceutically acceptable salt or solvate thereof, in the manufacture of a medicament for the treatment or prophylaxis of a reversible obstructive airways disease.

In a further aspect the invention provides a method of treatment or prophylaxis of inflammatory conditions which comprises administering to a host a therapeutically effective amount of a combination of an iNOS inhibitor and a COX-2 inhibitor as hereinbefore defined in association with a pharmaceutically acceptable adjuvant, diluent or carrier.

The invention is illustrated by the experimental data given below.

Assessment of anti-inflammatory activity in the rat carrageenan paw oedema (C. A. Winter et al, *Proc. Soc. Exp. Biol. Med.*, 1962, 111, 544)

Inflammation was induced in the right hind paw of 180-250g Charles River CD male rats by the injection of 0.1 ml of 1% carrageenan (Marine Colloids) in saline into the plantar region of the foot. Paw volume was measured by plethysmography before carrageenan injection and at 2, 4 and 6 hours after the intra-plantar injection. Paw oedema for each rat was calculated as the increase in paw volume over the initial paw volume measured prior to carrageenan injection. Inhibition of oedema for the treatments was calculated as a percentage inhibition of the mean absolute increase in foot volume in treated animals compared to control animals.

The rats were housed on sawdust and fasted overnight prior to the day of the experiment (water available ad libitum). The animals had free access to 5% glucose in water throughout the course of the experiment, and were re-fed after the 4 hour measurement. The ankle joint of each right hind paw was marked the day prior to the experiment to indicate the level to which the paw volume would be measured in the experiment.

Carrageenan was prepared the day prior to the experiment by suspending carrageenan in saline (1% w/v) and stirring vigorously on a magnetic stirrer for at least one hour. The suspension was stored at 4° C. until required and allowed to reach room temperature prior to use. The drugs were administered to groups of 6 rats 30 mins prior to carrageenan injection either orally (5 ml/kg) or subcutaneously (2 ml/kg). The COX-2 inhibitors were prepared for oral dosing in suspensions in 0.25% carboxymethylcellulose containing 1.5% Tween 80 (sonicated until dispersed). The iNOS inhibitor was dosed subcutaneously in 6% glucose in distilled water (dissolved by sonication for 5 min).

An INOS inhibitor or COX-2 inhibitor alone only produced a partial block of the inflammatory response, while a combination of the two produced a higher level of inhibition as shown in the Table below which shows anti-inflammatory activity 4 or 6 hours after administration of the carrageenan:

|  | Experiment 1 % inhibition | Experiment 2 % inhibition |
|---|---|---|
| 1. iNOS (n = 6) | 35 | 11 |
| 2. COX-2 (n = 6) | 35 | 32 |
| 1 and 2 (n = 6) | 74 | 63 |

1. iNOS = 1-(6-cyano-3-pyridylcarbonyl)-5',8'-difluorospiro[piperidine-4,2' (1'H)-quinazoline]-4'-amine hydrochloride (30 μmol/kg).
2. COX-2 = Celecoxib (3 mg/kg).

We claim:
1. A pharmaceutical combination comprising a COX-2 inhibitor or a pharmaceutically acceptable salt thereof and a compound of formula I:

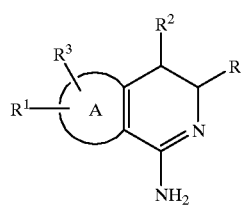

in which
R represents:
(i) phenyl, benzothiazolyl or a six membered heterocyclic aromatic ring containing 1 to 3 nitrogen atoms, which phenyl, benzo ring of the benzothiazolyl or heterocyclic aromatic ring is optionally substituted by $C_{1-6}$ alkyl, $C_{1-6}$ alkoxy, halogen, hydroxy, thio$C_{1-6}$ alkyl, benzyloxy, or a group —Q(CH$_2$)$_p$NR$^4$R$^5$; or
(ii) $C_{1-8}$ alkyl, $C_{3-8}$ cycloalkyl, $C_{2-8}$ alkynyl, piperidyl, $C_{7-14}$ phenylalkyl, which alkyl, cycloalkyl, alkynyl, or piperidyl is optionally substituted by a group —(CH$_2$)$_p$NR$^4$R$^5$, the phenylalkyl being optionally substituted by a group —(CH$_2$)$_p$NR$^4$R$^5$, $C_{1-6}$ alkyl, $C_{1-6}$ alkoxy, halogen or nitro; or
(iii) a 5 membered heterocyclic aromatic ring containing 1 to 3 heteroatoms independently selected from O, N or S, optionally substituted by $C_{1-6}$ alkyl, $C_{7-14}$ phenylalkyl or halogen; or
(iv) hydrogen or $C_{7-14}$ phenylalkynyl;
Q represents O, NR$^6$ or a bond;
R$^1$ represents hydrogen, $C_{1-6}$ alkyl, $C_{1-6}$ alkoxy, trimethylsilyl or halogen;
R$^2$ represents hydrogen, $C_{1-6}$ alkyl or phenyl optionally substituted by $C_{1-6}$ alkyl,
$C_{1-6}$ alkoxy, halogen or hydroxy;
R$^3$ represents hydrogen or halogen;
R$^4$, R$^5$ and R$^6$ independently represent hydrogen or $C_{1-6}$ alkyl,
or —NR$^4$R$^5$ together represents piperidyl, pyrrolidinyl or morpholinyl;

p represents an integer 1 to 5; and
A represents a thieno or benzo ring;
or a pharmaceutically acceptable salt thereof, wherein said combination has greater antiinflammatory efficacy as compared to the efficacy of said COX-2 inhibitor and said compound taken alone.

2. The combination according to claim 1 in which in the compound of formula (I) R is ethynyl, cyclopropyl, fluorophenyl, benzyloxyphenyl, thiomethylphenyl, methylphenyl, methoxyphenyl, chlorophenyl, furyl, thienyl, pyridyl, phenylethynyl, aminopropyloxyphenyl, aminoethylphenyl, aminopropylphenyl, thiazolyl, imidazolyl, methyl, ((dimethylamino)methyl)phenyl, propynyl, butylethynyl, benzylpyrrolyl, methylpyrrolyl, ethyl, cyclobutyl, hydroxyphenyl or propyl.

3. The combination according to claim 1 in which in the compound of formula (I) R$^1$ and R$^3$ are hydrogen or halogen.

4. The combination according to claim 1 in which in the compound of formula (I) R$^2$ is hydrogen.

5. The combination according to claims 1 in which the compound of formula (I) is
1-amino-3-(2-fluorophenyl)-3,4-dihydroisoquinoline; or
1-amino-3-phenyl-3,4-dihydroisoquinoline; or
1-amino-3-(4-(benzyloxy)phenyl)-3,4-dihydroisoquinoline; or
1-amino-3-(4-(methylthio)phenyl)-3,4-dihydroisoquinoline; or
1-amino-3-(4-(methyl)phenyl)-3,4-dihydroisoquinoline; or
1-amino-3-(3-(methyl)phenyl)-3,4-dihydroisoquinoline; or
1-amino-3-(4-(methoxy)phenyl)-3,4-dihydroisoquinoline; or
1-amino-5-methoxy-3-phenyl-3,4-dihydroisoquinoline; or
1-amino-3-(2-(chloro)phenyl)-3,4-dihydroisoquinoline; or
1-amino-3-(3-(chloro)phenyl)-3,4-dihydroisoquinoline; or
1-amino-3-(4-(chloro)phenyl)-3,4-dihydroisoquinoline; or
1-amino-5-chloro-3-phenyl-3,4-dihydroisoquinoline; or
1-amino-8-chloro-3-phenyl-3,4-dihydroisoquinoline; or
1-amino-3-(4-(fluoro)phenyl)-3,4-dihydroisoquinoline; or
1-amino-3-(3-(fluoro)phenyl)-3,4-dihydroisoquinoline; or
1-amino-5-fluoro-3-phenyl-3,4-dihydroisoquinoline; or
1-amino-8-fluoro-3-phenyl-3,4-dihydroisoquinoline; or
1-amino-6-bromo-3-phenyl-3,4-dihydroisoquinoline; or
1-amino-3-(2-(methyl)phenyl)-3,4-dihydroisoquinoline; or
1-amino-7-methyl-3-phenyl-3,4-dihydroisoquinoline; or
1-amino-5-methyl-3-phenyl-3,4-dihydroisoquinoline; or
1-amino-3-(2-furyl)-3,4-dihydroisoquinoline; or
1-amino-3-(3-furyl)-3,4-dihydroisoquinoline; or
1-amino-3-(2-thienyl)-3,4-dihydroisoquinoline; or
1-amino-3-(3-thienyl)-3,4-dihydroisoquinoline; or
1-amino-8-chloro-3-(2-furyl)-3,4-dihydroisoquinoline; or
1-amino-3-(3-pyridyl)-3,4-dihydroisoquinoline; or
1-amino-3-(4-pyridyl)-3,4-dihydroisoquinoline; or 1-amino-3-cyclopropyl-3,4-dihydroisoquinoline; or 1-amino-3-(2-(dimethylamino)methyl)phenyl-3,4-dihydroisoquinoline; or 1-amino-3-(3-(dimethylamino)methyl)phenyl-3,4-dihydroisoquinoline; or 1-amino-3-(2-benzothiazolyl)-3,4-dihydroisoquinoline; or 1-amino-8-chloro-3-(4-fluorophenyl)-3,4-dihydroisoquinoline; or 1-amino-3-(phenylethynyl)-3,4-dihydroisoquinoline; or 1-amino-8-methyl-3-phenyl-3,4-dihydroisoquinoline; or 1-amino-5-fluoro-3-(4-fluorophenyl)-3,4-dihydroisoquinoline; or 1-amino-8-fluoro-3-(4-fluorophenyl)-3,4-dihydroisoquinoline; or 1-amino-5,8-difluoro-3-(4-fluorophenyl)-3,4-dihydroisoquinoline; or 1-amino-6-fluoro-3-(4-fluorophenyl)-3,4-dihydroisoquinoline; or 1-amino-7-fluoro-3-(4-fluorophenyl)-3,4-dihydroisoquinoline; or 1-amino-3-ethynyl-3,4-dihydroisoquinoline; or 1-amino-3-(4-(3-aminopropyloxy)phenyl)-3,4-dihydroisoquinoline; or 1-amino-3-(3-(2-aminoethyl)phenyl)-3,4-dihydroisoquinoline; or 1-amino-3-(4-(2-aminoethyl)phenyl)-3,4-dihydroisoquinoline; or 1-amino-3-(3-(3-aminopropyl)phenyl)-3,4-dihydroisoquinoline; or 1-amino-3-(2-thiazolyl)-3,4-dihydroisoquinoline; or 1-amino-3-(2-imidazolyl)-3,4-dihydroisoquinoline; or 1-amino-3-(4-piperidyl)-3,4-dihydroisoquinoline; or 1-amino-3-methyl-3,4-dihydroisoquinoline; or 1-amino-3-(4-hydroxyphenyl)-3,4-dihydroisoquinoline; or 7-amino-5-phenyl-4,5-dihydrothieno[2,3-c]pyridine; or 7-amino-5-(3-pyridyl)-4,5-dihydrothieno[2,3-c]pyridine; or 7-amino-5-cyclopropyl-4,5-dihydrothieno[2,3-c]pyridine; or 7-amino-5-(3-furyl)-4,5-dihydrothieno[2,3-c]pyridine; or 7-amino-5-(2-furyl)-4,5-dihydrothieno[2,3-c]pyridine; or 7-amino-5-(2-thienyl)-4,5-dihydrothieno[2,3-c]pyridine; or 7-amino-5-(1-benzyl-2-pyrrolyl)-4,5-dihydrothieno[2,3-c]pyridine; or 7-amino-5-(1-methyl-2-pyrrolyl)-4,5-dihydrothieno[2,3-c]pyridine; or 7-amino-5-ethynyl-4,5-dihydrothieno[2,3-c]pyridine; or 7-amino-5-propynyl-4,5-dihydrothieno[2,3-c]pyridine; or 7-amino-5-(2-thiazolyl)-4,5-dihydrothieno[2,3-c]pyridine; or 7-amino-5-(3,3-dimethylbutynyl)-4,5-dihydrothieno[2,3-c]pyridine; or 7-amino-5-(phenylethynyl)-4,5-dihydrothieno[2,3-c]pyridine; or 7-amino-5-(cyclobutyl)-4,5-dihydrothieno[2,3-c]pyridine; or 7-amino-5-ethynyl-2-methyl-4,5-dihydrothieno[2,3-c]pyridine; or 7-amino-5-ethyl-4,5-dihydrothieno[2,3-c]pyridine; or 7-amino-5-propyl-4,5-dihydrothieno[2,3-c]pyridine; or 4-amino-6-phenyl-6,7-dihydrothieno[3,2-c]pyridine; or 4-amino-6-ethynyl-6,7-dihydrothieno[3,2-c]pyridine; or 4-amino-6-cyclopropyl-6,7-dihydrothieno[3,2-c]pyridine; or 7-amino-4,5-dihydrothieno[2,3-c]pyridine; or 4-amino-6,7-dihydrothieno[3,2-c]pyridine;

or pharmaceutically acceptable salts thereof.

6. A combination according to claim 1 in which the COX-2 inhibitor is Celecoxib, Meloxicam, L-745337, MK-966, L-768277, GR-253035, JTE-522, RS-57067-000, SC-58125, SC-078, PD-138387, NS-398, flosulide or PD-164387 or a pharmaceutically acceptable salt thereof.

7. A combination according to claim 1 in which the COX-2 inhibitor is Celecoxib or MK-966 or a pharmaceutically acceptable salt thereof.

8. A combination according to claim 1, comprising a pharmaceutically acceptable carrier.

9. A method of treatment of an inflammatory disease in a person suffering from or susceptible to such a disease, which method comprises administering to the person a therapeutically effective amount of a combination according to claim 1.

10. A pharmaceutical composition comprising a combination according to claim 1, and a pharmaceutically acceptable adjuvant, diluent or carrier.

* * * * *